(12) United States Patent
Husemann et al.

(10) Patent No.: US 9,695,391 B2
(45) Date of Patent: Jul. 4, 2017

(54) CONTAINER, TRANSPORT DEVICE, USE AND METHOD

(71) Applicant: Sartorius Stedim Biotech GmbH, Goettingen (DE)

(72) Inventors: Bernward Husemann, Goettingen (DE); Wolfgang Kahlert, Koerle (DE); Sebastien Chaussin, Aubagne (FR); Reiner Seitz, Helsa (DE)

(73) Assignee: Sartorius Stedim Biotech GmbH (DE)

( * ) Notice: Subject to any disclaimer, the term of this patent is extended or adjusted under 35 U.S.C. 154(b) by 28 days.

(21) Appl. No.: 14/764,281

(22) PCT Filed: Feb. 4, 2014

(86) PCT No.: PCT/EP2014/000284
§ 371 (c)(1),
(2) Date: Jul. 29, 2015

(87) PCT Pub. No.: WO2014/121918
PCT Pub. Date: Aug. 14, 2014

(65) Prior Publication Data
US 2015/0376563 A1    Dec. 31, 2015

(30) Foreign Application Priority Data

Feb. 5, 2013   (DE) .................. 10 2013 002 091

(51) Int. Cl.
*C12M 1/00*      (2006.01)
*C12M 3/00*      (2006.01)
(Continued)

(52) U.S. Cl.
CPC ............. *C12M 23/52* (2013.01); *B65G 67/04* (2013.01); *C12M 23/14* (2013.01); *C12M 23/26* (2013.01);
(Continued)

(58) Field of Classification Search
CPC ....... B65G 67/04; C12M 23/14; C12M 23/26; C12M 23/46; C12M 23/48; C12M 23/52;
(Continued)

(56) References Cited

U.S. PATENT DOCUMENTS

2007/0224676 A1    9/2007 Haq
2010/0255582 A1*   10/2010 Porter .................... C12M 23/26
                                                              435/401
(Continued)

OTHER PUBLICATIONS

International Search Report of Jun. 4, 2014.

*Primary Examiner* — Nathan Bowers
*Assistant Examiner* — Lydia Edwards
(74) *Attorney, Agent, or Firm* — Gerald E. Hespos; Michael J. Porco; Matthew T. Hespos

(57) ABSTRACT

One aspect relates to a container for inserting into a holding device, comprising: a wall that is flexible at least in some areas, which wall is squashed, at least in some areas, in a transport condition in a direction opposite to a stretching direction; a handling unit connected to the wall, which is designed to come into engagement with a complementary handling unit of a transport device; a securing unit which in a transport condition hinders stretching of the wall of the bioreactor container along the stretching direction, wherein the container can, when the securing unit is released, be extended at least in some areas along the stretching direction, as well as a transport device, a use and a method.

8 Claims, 14 Drawing Sheets

(51) Int. Cl.
   *C12M 1/06*   (2006.01)
   *C12M 1/34*   (2006.01)
   *B65G 67/04*  (2006.01)
   *F16M 11/04*  (2006.01)
   *F16M 11/08*  (2006.01)

(52) U.S. Cl.
   CPC ............ *C12M 23/46* (2013.01); *C12M 23/48* (2013.01); *C12M 27/02* (2013.01); *C12M 41/44* (2013.01); *F16M 11/046* (2013.01); *F16M 11/08* (2013.01)

(58) Field of Classification Search
   CPC ..... C12M 27/02; C12M 41/44; F16M 11/046; F16M 11/08; G11B 5/64
   See application file for complete search history.

(56) References Cited

U.S. PATENT DOCUMENTS

| | | |
|---|---|---|
| 2011/0038222 A1 | 2/2011 | Ludwig et al. |
| 2012/0282688 A1 | 11/2012 | Knight et al. |

* cited by examiner

CONTAINER, TRANSPORT DEVICE, USE AND METHOD

BACKGROUND

1. Field of the Invention

The invention relates to a container, a transport device for lifting and transporting the container and a method for inserting the container into a holding device.

2. Description of the Related Art

Containers that are flexible in some areas, such as for example bags, are used as bioreactor containers for process management or storage in particular in the pharmaceutical and biotechnological industries. Such containers may have a capacity for volumes of 1000 liters or more and are therefore folded together for transport in a space-saving manner. For use, the containers are mounted in a substantially rigid holding device that supports the wall of the container, so that the pressure acting on the wall of the container after the filling of the container is received by the holding device. As a rule, the wall of the container as such is not designed to be strong enough to hold the contents of the container after filling. In other words, the container would burst outside of the holding device during or after the filling process. Due to their size and their weight, it is very difficult or even impossible to handle the containers manually.

It is therefore an object of the invention to provide a container, a transport device for lifting and transporting the container and a method for inserting the container into a holding device, wherein improved handling of the container is made possible.

SUMMARY OF THE INVENTION

One aspect relates to a container for inserting into a holding device, comprising:
- a wall that is flexible at least in some areas, which wall is shortened in a transport condition in a direction opposite to a stretching direction at least in some areas;
- a handling unit connected with the wall, designed to come into engagement with a complementary handling unit of a transport device;
- a securing unit which, in the transport condition, hinders stretching of the wall of the container along the stretching direction, wherein the container can be extended along the stretching direction at least in some areas, when the securing means is released.

Advantageously, the securing means allows the container to be transported and/or to be held and lifted, whilst the container remains in the transport condition, i.e. in the shortened condition, and is therefore easier to handle due to its smaller size compared to a mounting condition in which the container is stretched. Further, the wall of the container may advantageously be mechanically stabilised by the securing unit, in particular in a preferred embodiment when the container is filled, for example with a fluid and/or a powdery, granular or flowable solid material.

The term "container" in terms of the application comprises containers, in particular bioreactor containers, with walls that are flexible in some areas, which may be used for example for receiving, mixing, storing and dispensing media, in particular sterile media.

To this end, the container comprises a fluid-tight wall that is flexible at least in some areas. In particular, the container has a wall that is formed from a film or a composite or laminate of a plurality of films. In other words, the container may be formed as a bag. The container is variable in its volume due to its variable extension along the stretching direction or its ability to be shortened and stretched. In particular, in its stretched mounting condition the container may have a volume that is larger by a factor of approx. 5, preferably larger by a factor of approx. 10 and particularly larger by a factor of approx. 20 than the volume of the container in the shortened transport condition.

In other words, the inner volume of the container may be minimal in the transport condition and may increase as the container is filled and may decrease again when it is emptied. For filling and emptying, the container may have at least one container opening. The at least one container opening is preferably formed as a fitting and/or a connector, so that fluid lines can be connected to the container in a simple manner by means of the at least one fitting.

Preferably, the container can be stretched and/or shortened substantially along exactly one stretching direction. In other words, during the transition from the transport condition to the mounting condition, the extension of the container remains substantially constant in two directions that are perpendicular to each other, which are oriented substantially perpendicularly to the stretching direction. In particular, the length of the extension in these two directions in the mounting condition may amount to approx. 50 percent to approx. 150 percent of the length of the extension in the transport condition. By contrast, the length along the stretching direction in the mounting condition may be more than approx. 200%, preferably more than approx. 500%, in particular more than approx. 1000% of the length in the stretching direction in the transport condition.

The container has a handling unit that is formed to be mechanically more rigid than the flexible wall of the container. Advantageously, the complementary handling unit of the transport device can grip the container in the area of the handling unit, without deforming the flexible wall of the container. Further, advantageously this does not place any mechanical stress on the flexible wall of the container, so that the risk of damage to the wall during transport and handling of the container is reduced.

The engagement between the complementary handling unit and the handling unit of the container may contain a form-fitting connection or a frictional connection or a force connection, so that a release of the container from the transport device is hindered or prevented. Preferably, the complementary handling unit can receive the handling unit of the container along an insertion direction at least in some areas and the handling unit can be grasped at least in some areas. In particular, the grasping of the handling unit may be carried out by way of a displacement of the complementary handling unit relative to the handling unit of the container along a lifting direction, which is oriented perpendicularly to the insertion direction. As a result of the grasping, the handling unit is hindered from being displaced against the insertion direction and from releasing itself from the complementary handling unit.

The container comprises a securing unit that holds the container in the transport condition. In other words, the securing unit is used to hinder or prevent an extension or stretching of the wall of the container along the stretching direction, in particular if the container is grasped and lifted by the handling unit by the transport device, so that the underside of the container does not rest but floats freely. The extension of the wall of the container may for example be carried out by unfolding or unsquashing. Correspondingly, the shortening of the container in a direction opposite to the stretching direction may be carried out by folding or squashing the wall of the container.

The securing unit may be formed to be substantially inelastic. In other words, the extension of the securing unit along a longitudinal extension direction of the securing unit is substantially constant irrespective of whether or not a force acts on the securing unit along this longitudinal extension direction. In particular, the securing unit stretches if a force of 1 kN is applied that is oriented along this longitudinal extension direction by less than approx. 5 percent, preferably less than approx. 1 percent of the length that the securing unit has in the unstressed condition. Therefore, the container may be stretchable or shortenable to a minor extent in the transport condition. For example, the length of the container in the transport condition along the stretching direction may be shortened or extended by a length of less than approx. 10 cm, preferably less than approx. 5 cm, in particular less than approx. 1 cm.

Regardless of the inelasticity, the securing unit may be formed to be flexible. In particular, the securing unit may be formed to be elastic in one direction that is oriented perpendicularly to the longitudinal extension direction in which the securing unit is formed to be inelastic.

In this context, the container is designed such that the handling unit is oriented, during the lifting and transporting of the container by the transport device, in particular during the insertion of the container into the holding device, in such a way that the handling unit is disposed at the top side of the container. The at least one securing unit surrounds the wall of the container at least in some areas, preferably completely, in order to hinder a displacement of the top side of the container relative to the bottom side of the container. It will be understood that also a plurality of in particular like or identical securing units may be provided. For example, the container may have two, three, four, five or more securing units.

Preferably, the at least one securing unit may be fixed to the handling unit. The weight of the flexible wall of the container can therefore be applied to the handling unit by means of the securing unit because the handling unit is formed to be substantially rigid.

The securing unit can be unsecured or released, so that the container, once the securing unit is unsecured or released, can extend along the stretching direction, and the volume of the container may remain constant when the container or the at least one container opening is closed in a fluid-tight manner, or the volume of the container may increase when the container, during or after the stretching, is filled or when the pressure inside the container is reduced. The stretching of the container may be carried out in particular exclusively due to the effect of gravity on the container. In particular, the handling unit of the container, which is preferably located at the top side of the container, may be kept in a constant position by the transport device whilst the container is stretched along the stretching direction, for example when the bottom side is displaced to the bottom due to gravity.

It will be understood that the container may also be rotated in such a way that the handling unit is located at the bottom side of the container, i.e. on the side that faces the bottom. It will further be understood that the securing unit hinders a stretching of the container in this case as well. However, for the sake of simplicity it is assumed in the present application that in the transport condition, the handling unit is located at the top side of the container.

Preferably, the container has at least one securing unit attachment area that can come into engagement with an associated complementary securing unit attachment area of the securing unit in order to hinder a displacement of the securing unit perpendicularly to the stretching direction.

Advantageously, by means of the engagement of the securing unit attachment area with the associated complementary securing unit attachment area it can be prevented that the securing unit is displaced relative to the wall of the container in such a way that the position of the wall can no longer be held or secured by the securing unit and the container would as a result no longer remain in the transport condition, but could be stretched in an unintended and uncontrolled manner at least in some areas.

It will be understood that the container may also comprise a plurality of securing unit attachment areas, for example two, three, four, five, six, seven or more securing unit attachment areas. In this context, the at least one complementary securing unit attachment area of the securing unit may be connected in a releasable or unreleasable manner to an associated securing unit attachment area. Preferably, the at least one securing unit attachment area may be formed on the outside of the wall of the container. In particular, the at least one securing unit attachment area may be formed to be more rigid than the flexible wall of the container.

Preferably, the at least one securing unit attachment area is provided on a side of the wall of the container that is opposite the handling unit along the stretching direction.

Advantageously, the securing unit may enclose the wall of the container and the securing unit may be fixed to the wall on two opposite sides of the container, in particular on the handling unit and the opposite securing unit attachment area. It will be understood that a plurality of securing unit attachment areas may be provided along a circumference of the container or the wall of the container. The at least one securing unit may then have a corresponding number of complementary securing unit attachment areas and may be provided along the circumference on the container in such a way that the securing unit attachment areas are each connected to an associated complementary securing unit attachment area or are fixed thereto in a releasable or unreleasable manner. By means of an unreleasable connection of the complementary securing unit attachment areas to the associated securing unit attachment areas, the securing unit is advantageously connected to the container in a captive manner, so that the securing unit can be reused after the use of the container, in order to secure the container after the container has been folded or squashed back together.

The at least one securing unit attachment area is preferably formed on a baseplate and the baseplate is preferably formed to be planar in at least some areas, but may also be formed to be curved. The baseplate is advantageously formed to be rigid and reinforces the wall in the area of the bottom of the container, so that the wall in the bottom area is advantageously protected from mechanical damage, for example during the insertion of the container into the holding device. The baseplate may in particular merely form the bottom of the container in some areas. For example, the baseplate may merely form less than approx. 50 percent or less than approx. 10 percent of the bottom of the container. Further preferably, the baseplate may also completely form the bottom of the container. In other words, the lateral extension of the baseplate may be substantially identical to the lateral extension of the container. In particular, the container may be designed for being placed on the bottom, and in the transport condition and/or in the mounting condition, merely the baseplate or the securing unit mechanically contacts the bottom or the base of the holding device, however not the flexible wall.

Preferably, the at least one securing unit is releasably connected to the handling unit. In particular, a release of the securing unit from the handling unit may allow the container to be transferred from the transport condition to the mounting condition.

Alternatively or in addition, the at least one securing unit may be releasably connected to the baseplate. In particular, a release of the securing unit from the baseplate may also allow the container to be transferred from the transport condition to the mounting condition.

Preferably, the securing unit is formed as a flexible, substantially non-stretchable strap. Preferably, the securing unit may also be formed as a flexible, substantially non-stretchable chain or cable. The strap or the chain or the cable may be substantially non-stretchable along the direction of the longitudinal extension and may be formed to be flexible or bendable perpendicularly to the extension direction. In other words, the length of the securing unit is substantially constant irrespective of whether a force acts on the securing unit or not. In particular, if a force of 1 kN is applied the strap or the chain or the cable stretches by less than approx. 5 percent, preferably less than approx. 1 percent of the length the strap or the chain or the cable has in the unloaded condition.

Preferably, the at least one complementary securing unit attachment area is formed as a hole in the strap. Correspondingly, the at least one securing unit attachment area may be formed as a projection or a hook that can engage in the hole. In particular, the strap can substantially completely surround the wall of the container, and in each of the two end areas of the strap, a hole is formed as a complementary securing unit attachment area. Correspondingly, two securing unit attachment areas may be provided on the handling unit, in particular on opposite sides of the handling unit, for example as hooks the strap may be hooked into. Further, at least one corresponding securing unit attachment area may be provided on the baseplate, for example as a projection, which can engage in an associated hole of the strap that may be formed centrally in the strap, in order to prevent the strap from sliding.

The securing unit is preferably fixed to the wall of the container or to one or more additional securing unit attachment areas at least in some areas. For example, the wall may be formed in two layers at least in some areas, with a through-opening being provided between the two layers, so that the securing unit, in particular in the form of a strap, may be passed through the through-opening in order to prevent a lateral sliding off. Preferably, the securing unit may be fixed to the wall of the container in the area of the bottom half of the container.

The strap of the securing unit and the wall of the container are preferably made from the same material. Advantageously, leftover pieces occurring during the production of the wall of the container may be used as a security means, as a result of which material savings and waste reduction are advantageously achieved. Further, in the case of sterile containers requiring approval it is not necessary to carry out the approval procedure again because the material of the wall will then already have been granted approval for use in sterile applications.

The wall of the container may in particular be made from a multi-layered material. The impermeability of the wall to a fluid, i.e. to a liquid, a gas or a mixture thereof, may be ensured by means of a fluid-tight layer, for example an internal layer of the wall. Moreover further layers may be provided, which are in particular impermeable to microorganisms, such as for example unicellular organisms, prions, bacteria, fungi, yeasts and/or viruses.

The internal layer is in contact with the inner volume of the container and therefore, during operative use of the container, with the fluid contained in the container, for example with educts or products of a biological, chemical or biochemical reaction that is to be carried out or has been carried out in the container. Therefore, the internal layer of the container is preferably made from a material that is biologically and/or chemically inert in respect of the reaction to be carried out, which means that the internal layer itself does not substantially react with the educts or products in a biological and/or chemical sense. The internal layer preferably consists of a polymer such as for example polyethylene (PE) and/or polypropylene (PP). Further preferably, at least the inside of the container that is surrounded by the internal layer can be sterilised, for example by gassing with ethylene oxide, by plasma treatment or gamma radiation, in order to ensure that the reaction can be initiated under sterile conditions. More preferably, the container openings may be formed as sterile connectors or may be fluidically connected to sterile connectors, for example via a tube. Preferably, an in particular sterile fluidic connection may be produced also via at least one tube that is welded to the container or the container opening and that may be closed at the distal end in a sterile manner. For producing the fluidic connection, the tube may also be welded to an external element, in particular in a sterile manner, and during the welding, a fluidic connection between the container and the external element may be formed. In the condition ready for use, in particular at least the inside of the container is sterile. Further preferably, the entire container is completely sterilised in the transport condition and is packed in a sterile manner. Preferably, the bioreactor container is intended for single use. In other words, the container may be a disposable article.

Preferably, the at least one securing unit is formed as at least one rigid connection element that surrounds the wall of the container at least in some areas. In particular, the securing unit may comprise a profile, a hollow profile, a pipe or a solid material from a metal or a plastic. The securing unit may here rigidly connect the handling unit to a securing unit attachment area, with the securing unit attachment area preferably being provided at the bottom or the baseplate of the container. The flexible wall of the container is then preferably provided between the handling unit and the securing unit attachment area, so that the container is prevented from stretching along the stretching direction by the rigid securing unit.

The rigid connection element is preferably unreleasably connected to the at least one securing unit attachment area and/or the baseplate. As a result, the securing unit may advantageously be connected to the container in a captive manner, so that the securing unit can, after usage of the container, be used for keeping the container, which is again in the squashed condition, in its squashed condition.

Preferably, the at least one securing unit is formed to be reusable in order to secure the bioreactor container after usage and after squashing it back together again in a direction opposite to the stretching direction S in the transport condition.

The handling unit preferably includes a shaft coupling in order to connect a shaft provided within the container to a drive provided outside of the container. Preferably, the container comprises a stirrer within the flexible wall, by means of which the contents of the container can be mixed through. In order to be able to squash the container, the shaft provided within the container is designed in a telescopic manner, for example in the form of at least two sub-shafts having different diameters, which can be pushed into each other in a telescopic manner. In particular, the shaft may be designed such that the shaft is pushed apart as a result of gravity when the shaft is vertically oriented and is held by its top end.

The shaft can penetrate through the wall of the container in the area of the shaft coupling, and the penetration opening in the wall is closed in a fluid-tight and preferably sterile manner. The shaft coupling is expediently provided in the rigid area of the handling unit. The shaft coupling may preferably be designed in such a way that it comes into form-fitting engagement with a drive. Alternatively or in addition, the force transmission between the drive and the shaft coupling may also be carried out magnetically. In this case, the force-locking coupling between the shaft and the drive may advantageously also be achieved in a contact-free manner, so that the shaft advantageously does not have to pass through the wall of the container, as a result of which fluid-tightness and sterility of the container can be achieved in a simple manner.

One aspect relates to the use of a securing device, in order to keep a container, in particular a container according to the invention as described above or a preferred embodiment thereof, having a wall that is flexible at least in some areas, which in a transport condition is shortened at least in some areas in a direction opposite to a stretching direction, in this transport condition, wherein the securing device has at least one complementary securing unit attachment area that is in engagement with an associated securing unit attachment area of the container. In particular, a securing device formed as a strap may be used, which has holes as a complementary securing unit attachment area.

One aspect relates to a transport device for lifting and transporting a container using a handling unit, in particular a container according to the invention or a preferred embodiment thereof, wherein the transport device comprises:
 a complementary handling unit that is designed to come into engagement with the handling unit of the container;
 an optional rotation device that can be used to rotate the complementary handling unit about a horizontal axis.

A further aspect relates to an arrangement of a transport device according to the invention with a container according to the invention that is provided thereon.

Advantageously, the transport device can be used to handle, transport and insert the container into the holding device in a simple manner.

The complementary handling unit is preferably formed with shapes matching, at least in some areas, that of the handling unit of the container. In particular, it must be possible to insert the handling unit of the container, at least in some areas, along an insertion direction into a recess of the complementary handling unit. In particular, the complementary handling unit may be formed to be fork-shaped or as a clamp, and the handling unit of the container can be inserted between the two arms of the fork or into the clamp.

The handling unit can preferably be locked in the complementary handling unit. In other words, a locking unit may be used to prevent the handling unit from being displaced in the direction opposite to the insertion direction relative to the complementary handling unit. For example, the locking unit can engage, at least in some areas, in the handling unit inserted into the complementary handling unit and/or can close the insertion opening of the complementary handling unit, once the handling unit has been inserted. The locking unit may be formed for example as a pivotable bracket that is pivoted, at least in some areas, around the inserted handling unit. The pivotable bracket may then be fixed in the closed position, once the complementary handling unit has been closed by means of a screw, in particular by means of a wing screw or a wing nut that can be rotated with or without the aid of a tool.

Alternatively or in addition, the complementary handling unit may have a magnetic locking unit that attracts a complementary magnetic locking unit of the handling unit of the container and magnetically fixes it thereby, so that the container is magnetically locked in the complementary handling unit.

It is further preferred if the complementary handling unit engages in a cantilever extension, a recess or a projection of the handling unit, so that the container can be lifted, lowered and/or rotated using the transport device, without a relative displacement between the complementary handling unit and the handling unit occurring or without the container releasing itself from the transport device.

The transport device preferably comprises a motorized lifting device that can displace the complementary handling unit along the lifting direction, in particular along the vertical, in particular by a distance of more than approximately one meter, preferably by a distance of more than approximately two meters and in particular by a distance of more than approximately three meters.

The transport device preferably comprises a motorized rotary device, by means of which the complementary handling unit, including a container held thereon, can be rotated about the horizontal axis. The horizontal axis is preferably oriented parallel to the insertion direction. The rotation device can rotate the complementary handling unit preferably by more than approx. 90 degrees, preferably by more than approx. 170 degrees and in particular by more than approx. 270 degrees. Particularly preferably, the rotation device allows one or more complete revolutions of the complementary handling unit about the horizontal axis.

The transport device can preferably be traversed, in particular traversed in a motorized manner. To this end, the transport device may include a plurality of wheels, and preferably at least one wheel may be connected to a drive. The drive may for example be electric.

One aspect relates to a method for inserting a squashable container that is flexible at least in some areas, in particular a container according to the invention or a preferred embodiment thereof, into a holding device, wherein the container comprises:
 a handling unit,
 a securing unit that hinders unfolding of the container, and
 wherein the method comprises the following steps:
 providing the container in a transport condition in which the container is squashed together in a direction opposite to a stretching direction at least in some areas;
 fixing the handling unit of the container to a complementary handling unit of a transport device, in particular of a transport device according to the invention or a preferred embodiment thereof;
 displacing the transport device, wherein the container is introduced into the holder at least in some areas;
 releasing the securing unit, as a result of which the container is unfolded along the stretching direction at least in some areas, so as to be transferred from the transport condition into a mounting condition; and
 releasing the handling unit from the complementary handling unit.

Advantageously, the container may be inserted into the holding device in a simple manner. The container is provided in the transport condition, for example on a transport pallet that is stored in a storage room. The container is preferably packaged in a sterile manner. Further preferably, the container may be stored with the handling unit oriented downwards and may be provided such that the securing unit is not mechanically stressed when the container is grasped by the handling unit and lifted. On the other hand, it is also possible to store the container oriented in such a way that the handling unit is located at the top, and the securing unit advantageously prevents the container from extending whilst being lifted, in particular by means of the transport device, along the stretching direction. However, in this case the securing unit will be exposed to mechanical stress or strain during lifting, because the weight of the flexible wall of the container and the optionally extendable shaft in the inside of the container acts on the securing unit.

It will be understood that the removal of the sterile packaging of the container may be carried out before or after the lifting of the container. Similarly, the release of the securing unit may be carried out before or after the lifting and before or after the optional rotation of the container.

Preferably, the container is moved in the transport condition by means of the transport device from the storage place of the container to the holding device and is vertically lifted to such a degree that the container can be placed in the holding device, in particular from the top. The storage place and the holding device may be physically separated from each other, for example by a gate or by a sterile sluice. Alternatively, the container may also be laterally inserted into the holding device, if the holding device has a corresponding lateral opening in the wall of the holding device. For example, the holding device may have a lateral door, through which the container can be introduced into the holding device and which can be closed once the container has been introduced.

For transporting, the container is fixed to the complementary handling unit of the transport device by means of the handling unit. The fixing may be carried out using magnetic attraction, clamping, screwing, a bayonet fitting, or in a similar manner. The container can then be moved by the transport device from the storage place of the container to the holding device and can be inserted therein at least in some areas. In particular, the holding device may only have a top opening, through which the container can be inserted. Therefore, the container may be vertically lifted by the transport device to such a degree that the container can be introduced into the holding device from the top. In order to ensure that the container has to be lifted as little as possible, the release of the securing device can preferably be carried out when the container is already located above the opening of the holding device. As a result of the release of the securing device, the container is stretched and/or unfolded by the effect of gravity at least in some areas along the stretching direction, in particular along the vertical, and thus preferably into the holding device. Optionally, the container may be lowered down further after the unfolding by means of the transport device, so as to be correctly placed in the holding device.

In the preferred case in which the container has an element with a length that is variable along the stretching direction, in particular a shaft of a stirrer, the length-variable element is stretched along the stretching direction after the release of the securing device, in particular merely due to the effect of gravity.

The complementary handling unit can then be released from the handling unit of the container, in order to remove the transport device.

The method may include the additional steps of squashing and/or folding the container after usage in a direction opposite to the stretching direction (S) and of fixing the securing unit, as a result of which the container is transferred back into the transport condition. Advantageously, after use, for example carrying out a biotechnological process, the container may be transported in a space-saving manner and/or discarded. In other words, the securing unit remains intact during release, so that the securing unit can be reused.

After release, the released securing unit may continue to be fixed to the container and/or may be located between the container and the inner wall of the holding device, so that the securing unit is, after usage of the container, advantageously available for securing the container again. Preferably, the step of fixing the securing unit may be carried out on the holding device. In particular, the holding device may include, in correspondence with the container, at least one securing unit attachment area to which the securing unit may be fixed.

In case the securing unit is formed as a strap, for example hooks or projections may be provided on the holding device and associated holes may be formed in the strap, by means of which the strap may be hooked or fixed to the hook or the projection. Alternatively or in addition, the strap may be clamped between the flexible container wall and the inner wall of the holding device, in particular after filling the container, and may protrude beyond or hang over the edge of the opening of the holding device.

In case the at least one securing unit is formed as a rigid connection, for example as a rod or a pipe, the securing unit may be clamped between the flexible container wall and the inner wall of the holding device, in particular after filling the container, and the rigid securing unit pushes into the wall of the flexible container in some areas. Especially if the container is used with a stirrer provided therein, the flow cross section of the fluid stirred in the container is locally reduced during the stirring in the area of the wall pushed in by the securing unit, so that in these places, the flow rate is locally increased, as a result of which turbulences are advantageously formed which lead to an improved mixing of the fluid.

After use, the container, which may preferably be a disposable container, is again fixed to the transport device by means of the handling unit and is lifted out of the holding device. In the course of this, the container may optionally be squashed in a direction opposite to the stretching direction again before and after being lifted out and may be secured in the squashed condition by means of the at least one securing unit.

Preferred embodiments of the present invention will be explained below by way of example with reference to the attached drawings. Individual features of the preferred embodiments shown may be combined into further preferred embodiments.

BRIEF DESCRIPTION OF THE DRAWINGS

FIG. 1b shows a section through the container shown in FIG. 1a.

FIG. 1d shows a top view of the container shown in FIG. 1a.

FIG. 2b shows a lateral view of the assembly shown in FIG. 2a.

FIG. 2d shows a top view of the assembly shown in FIG. 2a.

FIG. 3b shows a lateral view of the transport device shown in FIG. 3a.

FIG. 4b shows a lateral view of the arrangement shown in FIG. 4a.

FIG. 4d shows a top view of the arrangement shown in FIG. 4a.

FIG. 5b shows a section through the container shown in FIG. 5a.

FIG. 5d shows a top view of the container shown in FIG. 5a.

DETAILED DESCRIPTION

Figure 1A:
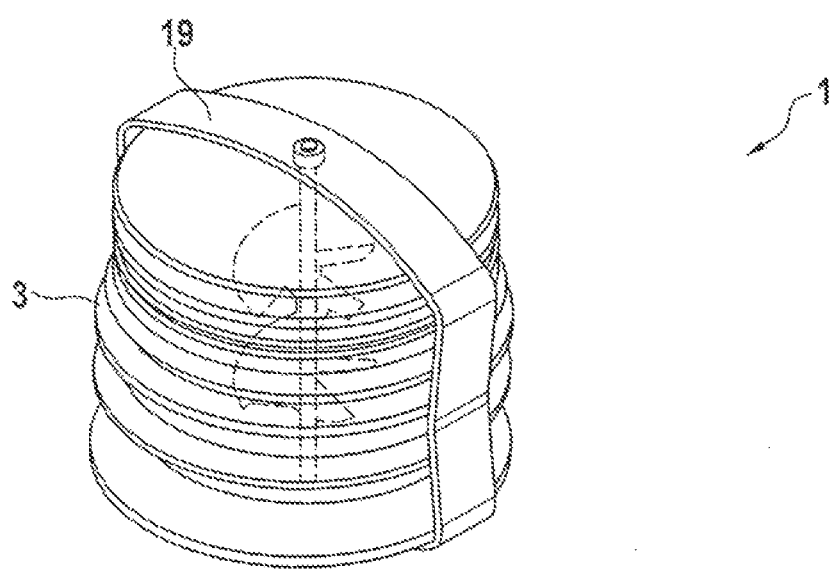
FIG. 1a shows a perspective view of a preferred embodiment of a container in the transport condition.
Figure 1B:
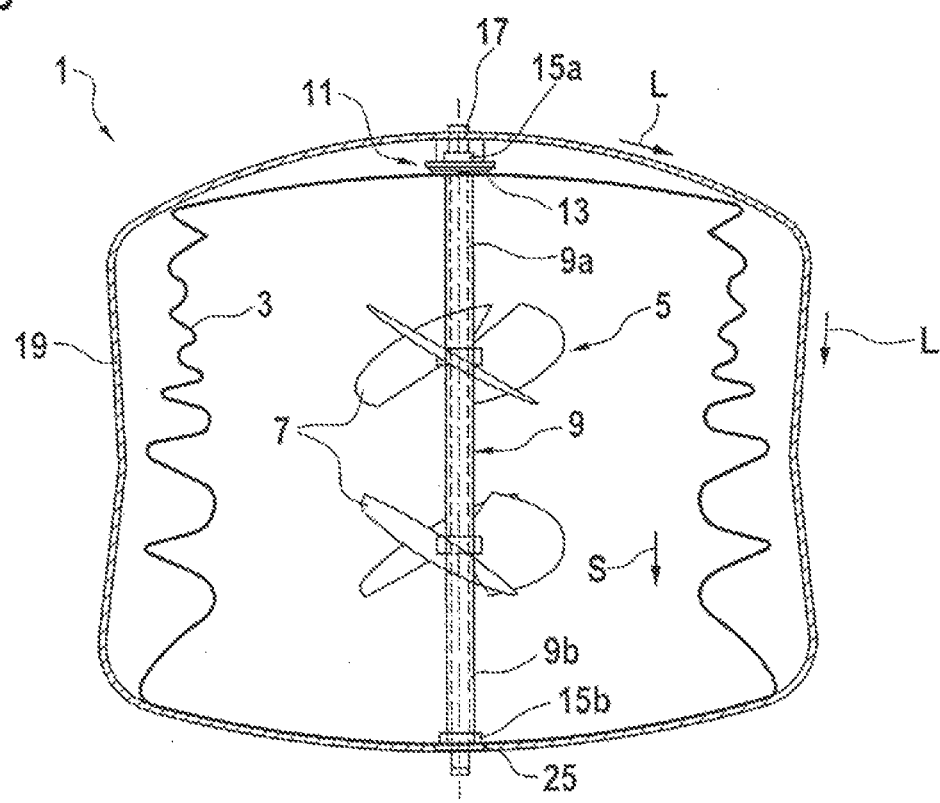
Figure 1C:
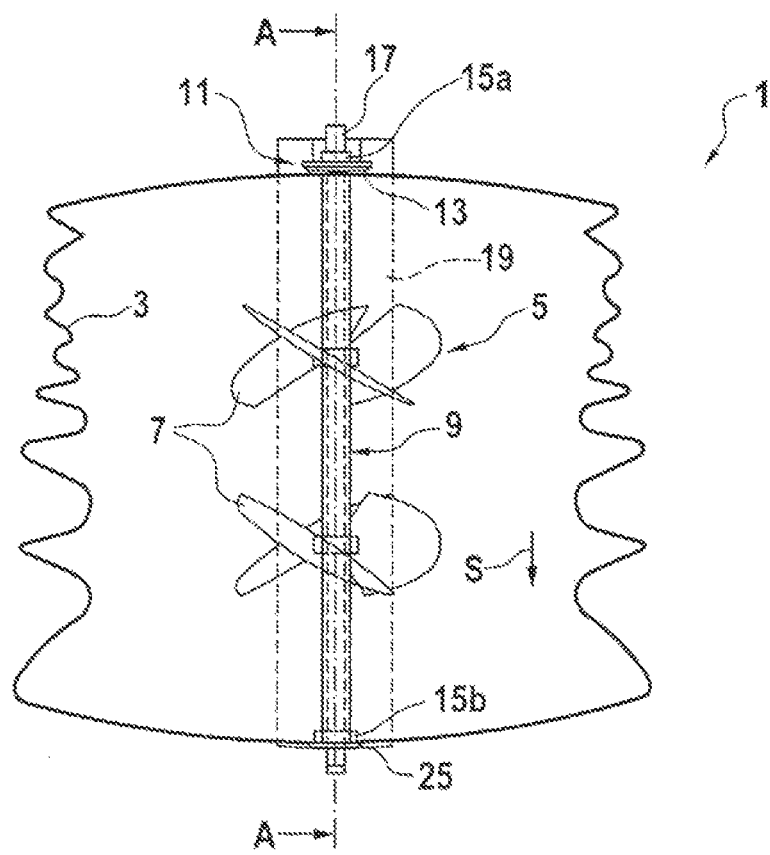
FIG. 1c shows a further section through the container shown in FIG. 1a, which is orientated perpendicular to the section shown in FIG. 1b.
Figure 1D:
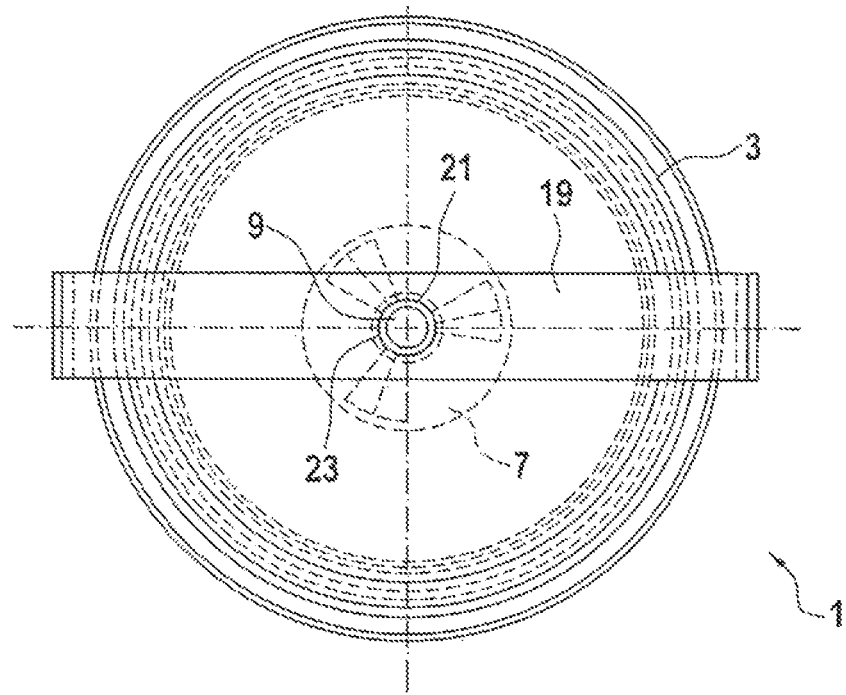
Figure 2A:
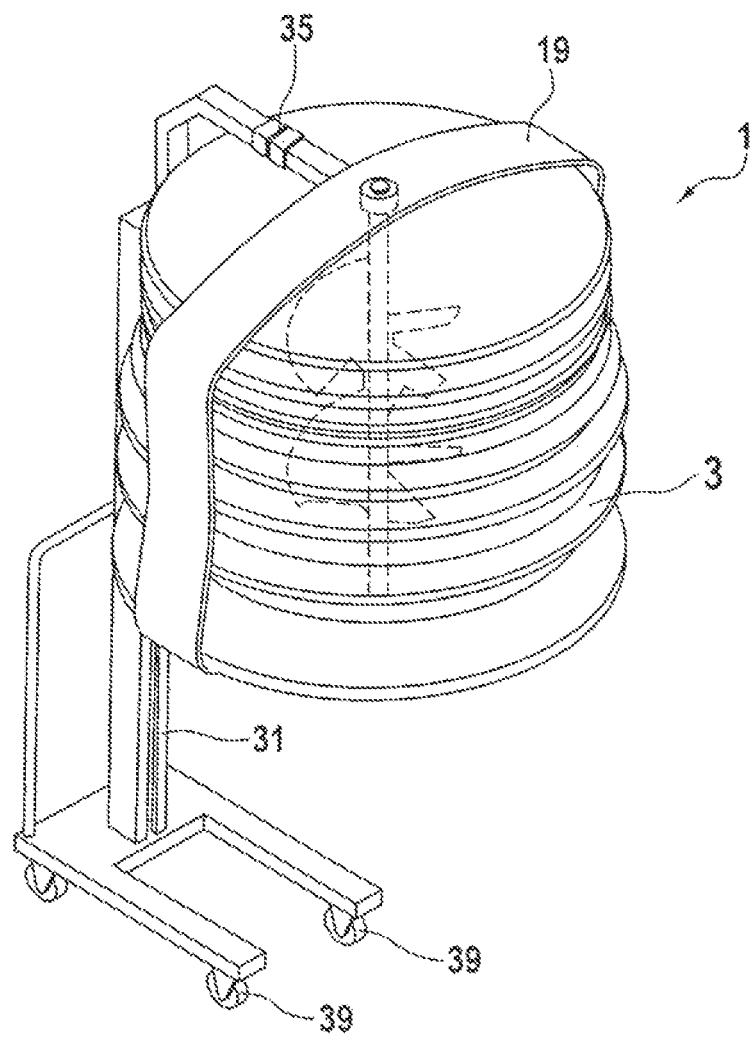
FIG. 2a shows a perspective view of an arrangement of a preferred embodiment of a transport device with an attached container in the transport condition.
Figure 2B:
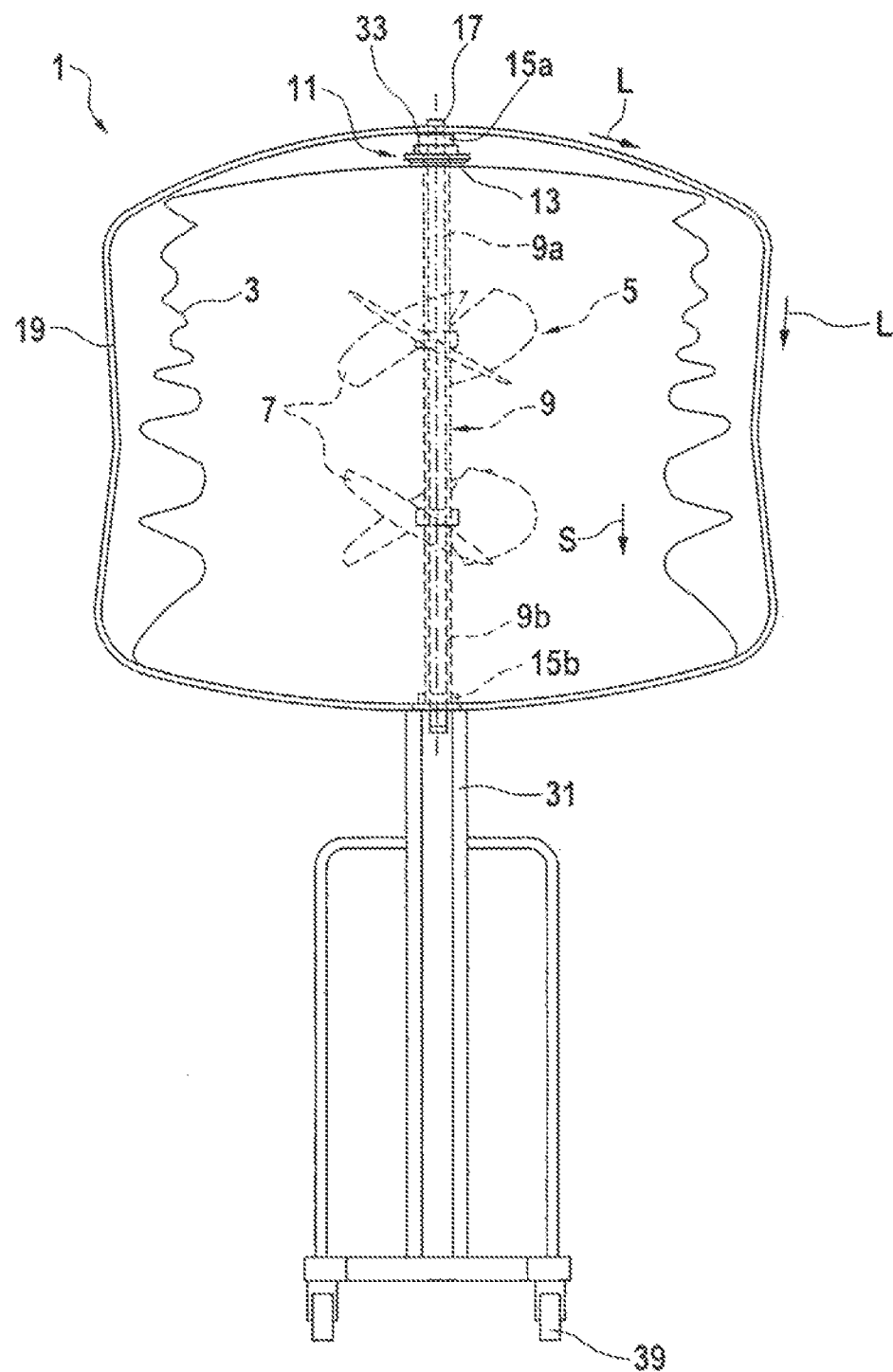
Figure 2C:
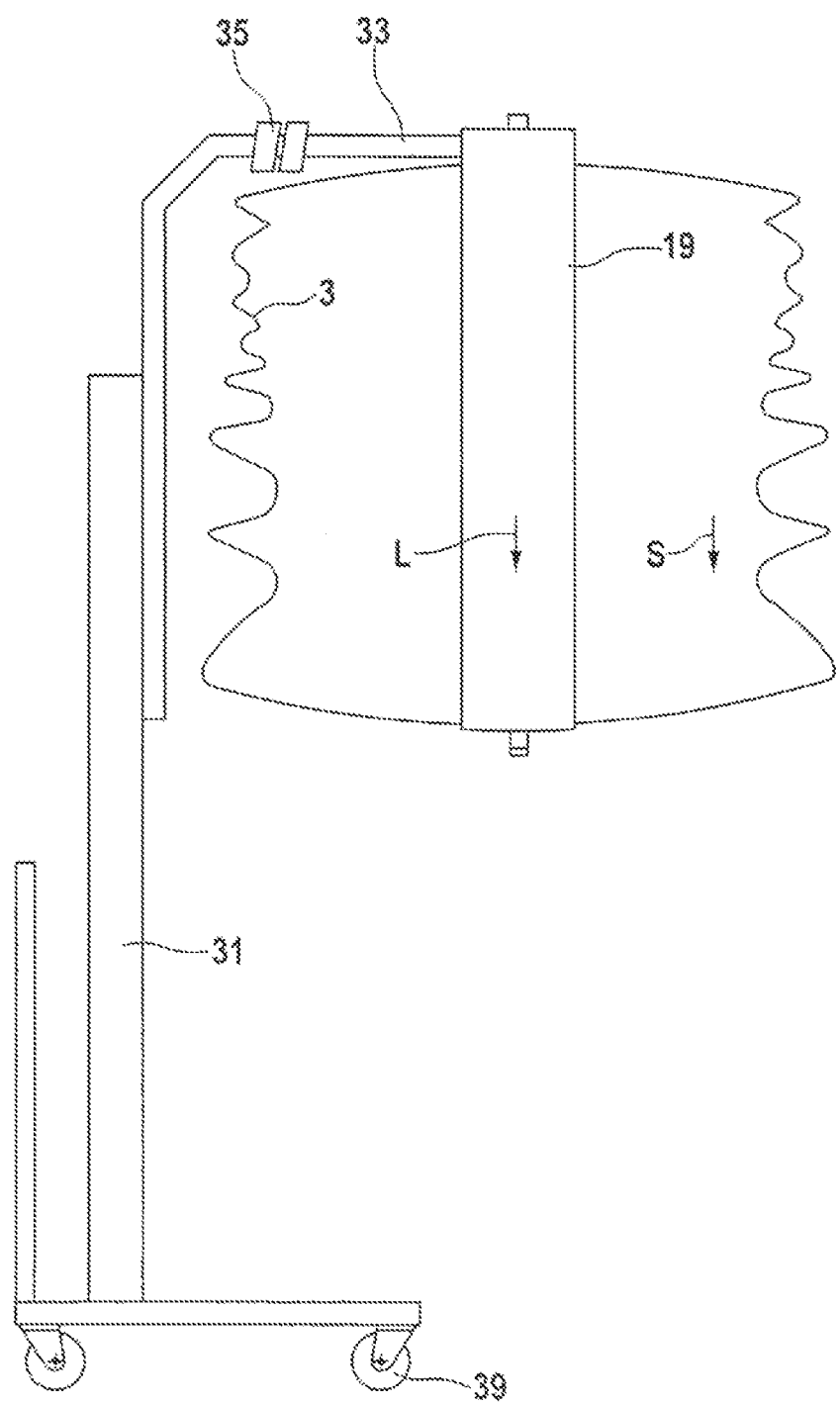
FIG. 2c shows a lateral view of the assembly shown in FIG. 2a, which is orientated perpendicularly to the lateral view shown in FIG. 2b.
Figure 2D:
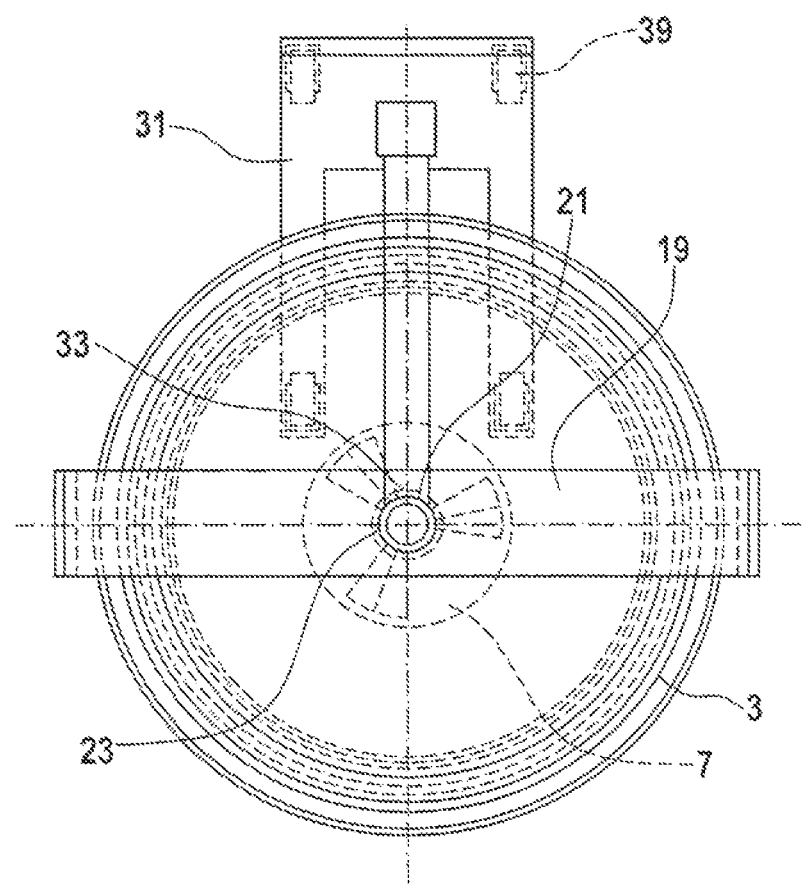

FIGS. 1a to 1d show various views of a preferred embodiment of a container 1 in the transport condition. The container may preferably be formed as a "bioreactor container". The container 1 comprises a wall 3 that is flexible at least in some areas and is for example designed for receiving, mixing, storing and dispensing fluids, in particular sterile fluids or media under sterile conditions. The wall 3 comprises at least one flexible, fluid-tight layer, so that a variable inner volume of the container 1 is enclosed by the wall 3. The wall 3 may be composed of a plurality of layers, which may at least partially be connected to each other in particular by laminating and/or gluing and/or welding. The inner volume of the container 1 can be fluidically connected via container openings (not shown) with the environment or with further elements such as for example fluid lines. It will be understood that the wall 3 may be formed stiffened or rigid in particular in the area of the container openings, so that the container openings are stable in shape and any fittings and connectors connected thereto will remain tight. The container 1 may be filled and emptied via the container openings.

The container 1 shown has a substantially cylindrical shape. It will be understood that the container 1 may also have a cuboid, a tetrahedral, a spherical, a prism-shape or any other desired shape.

The wall 3 that is flexible at least in some areas is shortened, at least in some areas, in the transport condition in the direction opposite to a stretching direction S, in particular squashed or folded, so that its dimensions are reduced along the stretching direction S. The container further comprises a stirrer 5 inside of the flexible wall 3, so that the content of the container can be mixed or agitated by means of the stirrer 5. The stirrer preferably comprises one or more (e.g. two) stirrer blades or wings 7, which are connected to a shaft 9 of variable length. The length-variable shaft 9 is preferably designed as a telescopic shaft 9, for example in the form of at least two sub-shafts 9a, 9b of different diameters, which can be pushed relative to each other (in particular at least partially pushed into each other in a telescopic manner), in order to be able to shorten the container 1 in the direction opposite to the stretching direction S.

The container 1 further has a handling unit 11 that is connected to the wall 3. The handling unit 11 is designed in such a way that it comes into engagement with a complementary handling unit 33 (shown in FIGS. 3a to 3c) of a transport device 31. As a result, the container 1 may be fixed to a transport device 31 (also shown in FIGS. 3a to 3c) by means of the handling unit 11, so as to be able to lift and/or transport the container 1. To this end, the handling unit 11 is in particular formed to be mechanically more rigid than the flexible wall 3 of the container 1. In particular, the handling unit 11 is formed to be so rigid and non-deformable that the complementary handling unit 33 of the transport device 31 can grasp or take up the container 1 by the handling unit 11, without deforming the flexible wall 3 of the container 1.

In the preferred embodiment shown, the handling unit 11 is provided on a through-opening 13 for the shaft 9, wherein the through-opening 13 is closed in the wall 3 in a fluid-tight and preferably sterile manner. Further, a shaft bearing 15a is provided in or on the through-opening 13, in which bearing the shaft 9 is rotationally supported.

Above the shaft bearing 15a and outside of the inner volume enclosed by the wall 3 of the container 1, a shaft coupling 17 is connected to the shaft 9, which can come into a form-fitting and/or force-fitting engagement with a drive (not shown), in order to drive the stirrer 5. As an alternative to the shaft coupling 17 shown in FIGS. 1a to 1d, also a magnetic force transmission between the drive and the shaft coupling may be realized. In this case, the shaft coupling may advantageously be provided within the inner volume of the container 1 that is enclosed by the wall 3, as a result of which advantageously a complex sealing of the shafts passing through the wall may be eliminated because the shaft is completely located within the inner volume. The coupling between the shaft and the drive is in particular realized in a substantially contact-free manner.

The container 1 further comprises at least one securing unit 19, which in the transport condition at least partially or in some areas prevents the wall 3 of the container 1 from unfolding along the stretching direction S. The at least one securing unit 19 is fixed to the handling unit 11 preferably in a releasable manner, so that a release of the securing unit 19 from the handling unit 11 allows a transfer of the container from the transport condition into the mounting condition.

In the preferred embodiment shown, exactly one securing unit 19 is provided which is implemented as a flexible, substantially non-stretchable strap 19. However, it will be understood that also two or more securing units 19 or straps 19 may be provided. The at least one strap 19 surrounds the wall 3 of the container 1 at least in some areas, preferably completely, along a circumference of the container 1, in order to hinder or counteract a displacement of the top side of the container 1 relative to the bottom side of the container, i.e. a stretching of the container along the stretching direction S. If the container is grasped and vertically lifted by the handling unit 11, the force of the weight of the flexible wall 3 and/or of the stirrer 5 acts on the strap 19. The strap 19 is substantially non-stretchable along the longitudinal extension direction L of the strap 19 and is formed to be flexible or bendable perpendicularly to the longitudinal extension direction L. Thus, the length of the strap 19 is preferably substantially constant irrespective of any mechanical load, i.e. irrespective of whether the container 1 is lifted by the handling unit 1 or not. As a result, the container 1 may be lifted in the squashed condition. As a result, the at least one strap 19 allows the container 1 to be lifted and transported in the shortened transport condition.

The at least one strap 19, which forms the securing unit 19, and the wall 3 of the container 1 are preferably made from the same material. Advantageously therefore, any leftover pieces that occur during the production of the wall 3 of the container 1 may be used as a securing unit. A further advantage is that a container 1 that has already been approved as a sterile container or as a bioreactor container does not need to be approved again if the preferred securing unit is used, because in this case, the material of the wall and thus the material of the securing unit has already been approved for use in sterile applications.

The container 1 may preferably have an inner volume with a capacity of more than approx. 1000 liters, further preferred of more than 3000 liters, in particular of more than approx. 5000 liters. For example, containers 1 with an internal volume of approx. 6000 liters are technically already feasible. Such a container 1 may be provided with a stirrer 5 (such containers 1 are also known as a "mixing bag").

Alternatively or in addition, the container 1 may, at least partially, also be filled, or may already have been filled in the transport condition, with a powdery or flowable solid material (such containers 1 are also known as a "mixing bag").

The container 1 may have at least one, preferably two, three or more, securing unit attachment areas 21 that can be brought into engagement with an associated complementary securing unit attachment area 23 of the securing unit 19 or of the strap 19, in order to prevent a displacement of the strap 19 perpendicularly to the longitudinal direction L of the strap 19. As a result, it is further prevented that the securing unit 19 or the strap 19 is displaced relative to the wall 3 of the container 1 in such a way that the position of the wall 3 can no longer be held or secured by the securing unit or the strap 19 and the container 1 stretches in an uncontrolled manner.

In the preferred embodiment shown, the strap 19 is provided with at least one hole 23 as the preferred complementary securing unit attachment area 23, and the handling unit 11 and/or the shaft 9 extend(s), at least in some areas, through this hole 23. The handling unit 11 may here at the same time act as a securing unit attachment area 21 in order to fix the strap at this point of the container 1.

At least one further securing unit attachment area 21 is provided on one side or in a lateral area of the wall 3 of the container 1, which side is opposite the handling unit 11 along the stretching direction S. At this point, the wall 3 is provided with a baseplate 25 that forms an area of the bottom of the container 1 and includes a further shaft bearing 15b next to the securing unit attachment area 21, through which or on which the shaft 9 is rotationally supported. Compared to the flexible wall 3, the baseplate 25 is formed to be relatively rigid. The complementary securing unit attachment area 23 of the strap 19, which is associated with the at least one securing unit attachment area 21 of the baseplate 25, may also be formed as a hole 23 in this strap 19. The strap 19 may be formed to be continuous or closed, so that it has to be cut for releasing and stretching the container.

The strap 19 preferably has two ends, with a complementary securing unit attachment area 23 or a hole 23 being formed in each end section of the strap 19. Correspondingly, one or two securing unit attachment areas 21, for example one or two projections or hooks or a protruding area of the shaft bearing 15b, may be provided on the bottom side of the container 1 or on the baseplate 25, so that the end sections of the strap 19 with the holes 23 may be fixed together to a securing unit attachment area 21 and to an associated securing unit attachment area 21, respectively.

FIGS. 2a to 2d show various views of the preferred embodiment of a transport device 31 with a container 1 fixed thereto in the transport condition. The transport device 31 has a complementary handling unit 33 which is designed to come into engagement with the handling unit 11 of the container. The transport device may further include a rotation device 35, by means of which the complementary handling unit 31 can be rotated about a horizontal axis. The rotation device 35 allows the container 1 to be stored and/or transported in a rotated condition, in particular head first, i.e. with the handling unit 11 facing the bottom, and to be turned around by means of the rotation device 35 once the container has been picked up. There is no need for the rotation device 35 if the container is stored in the correct orientation.

Figure 3A:
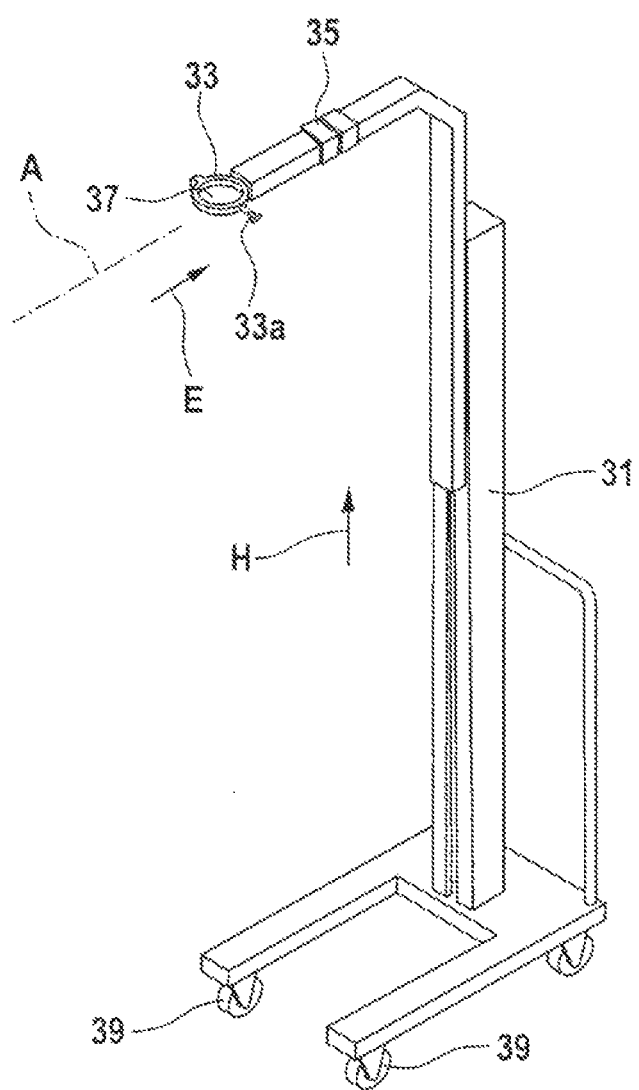
FIG. 3a shows a perspective view of an arrangement of a preferred embodiment of a transport device.
Figure 3B:
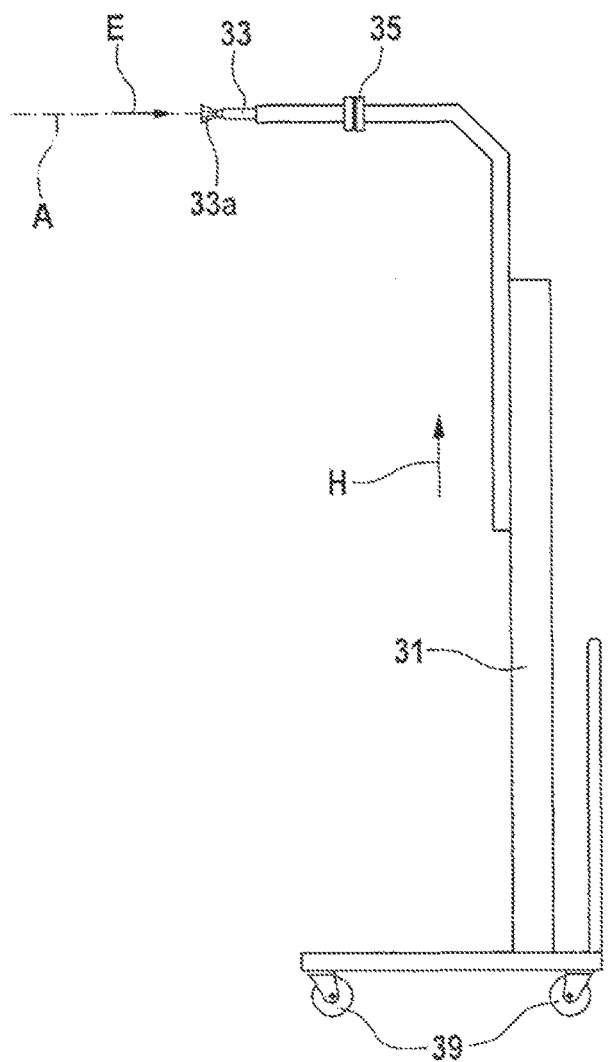
Figure 3C:
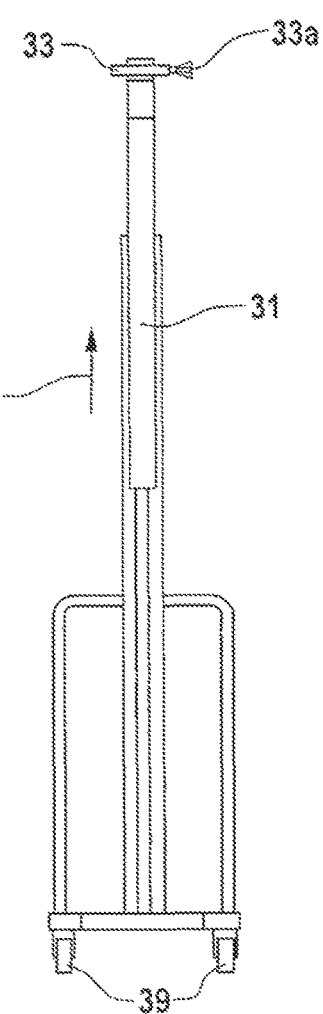
FIG. 3c shows a lateral view of the transport device shown in FIG. 3a, which is orientated perpendicularly to the lateral view shown in FIG. 3b.
Figure 4A:
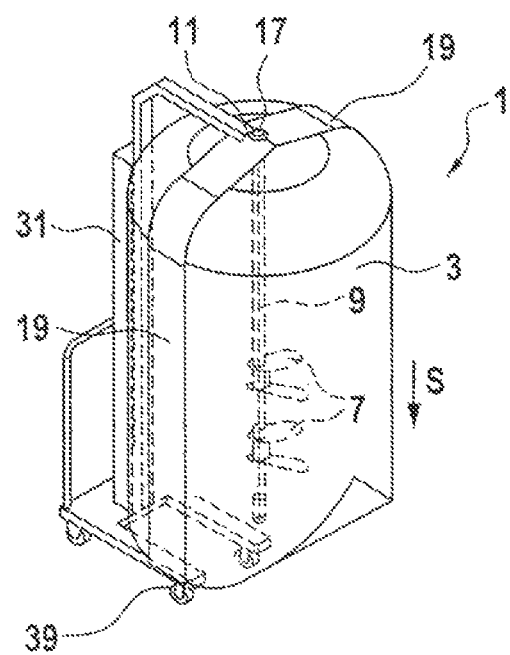
FIG. 4a shows a perspective view of an arrangement of a preferred embodiment of a transport device with an attached container in the mounting condition.
Figure 4B:
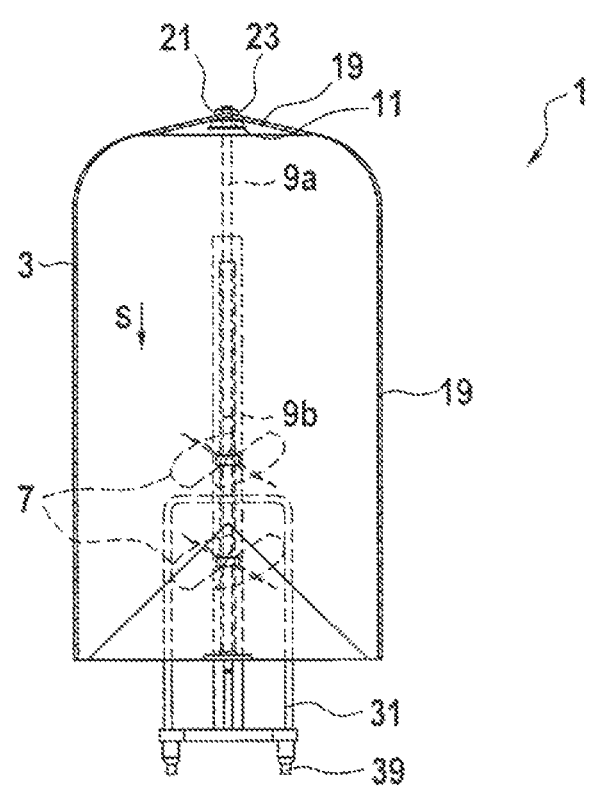
Figure 4C:
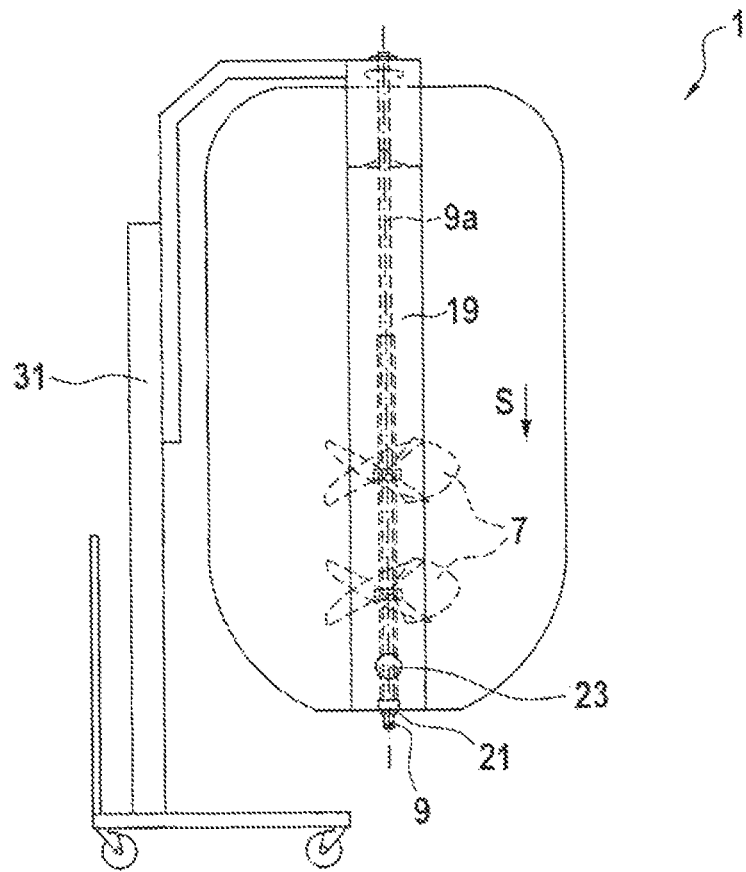
FIG. 4c shows a lateral view of the arrangement shown in FIG. 4a, which is orientated perpendicularly to the lateral view shown in FIG. 4b.
Figure 4D:
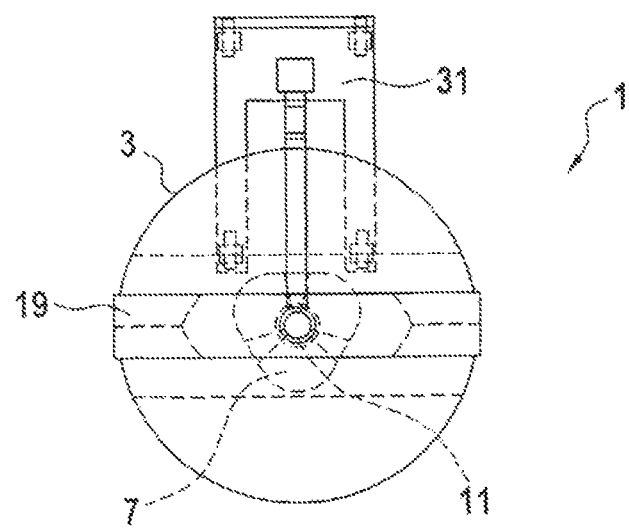
Figure 5A:
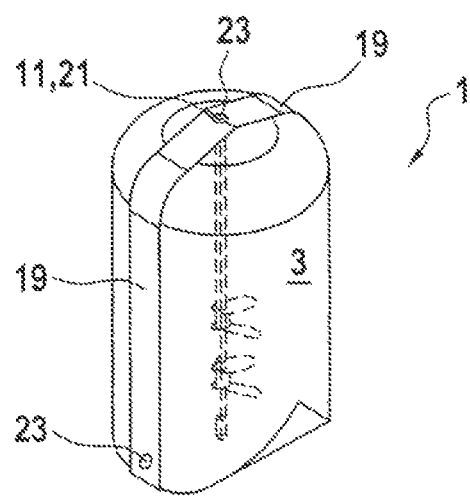
FIG. 5a shows a perspective view of a preferred embodiment of a container in the mounting condition.
Figure 5B:
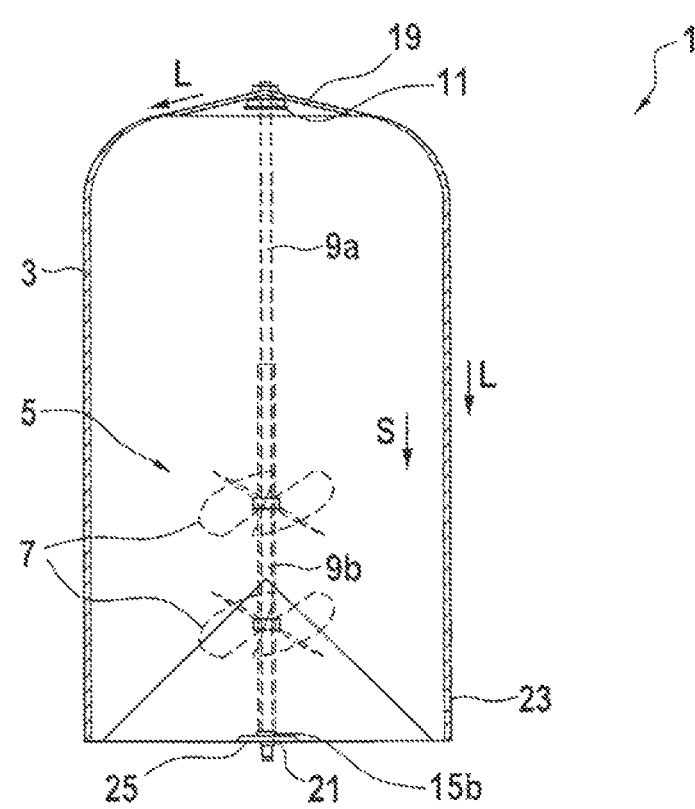
Figure 5C:
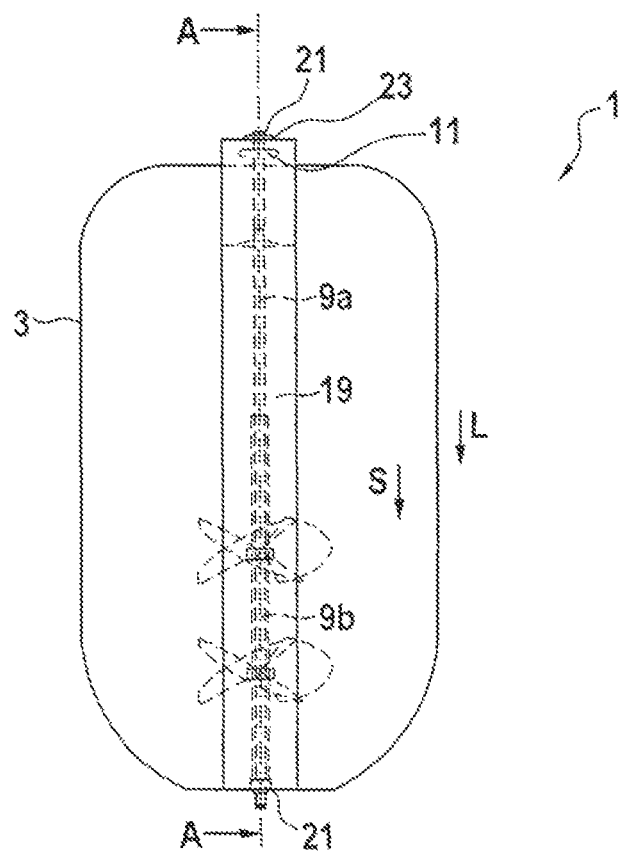
FIG. 5c shows a further section through the container shown in FIG. 5a, which is orientated perpendicularly to the section shown in FIG. 5b.
Figure 5D:
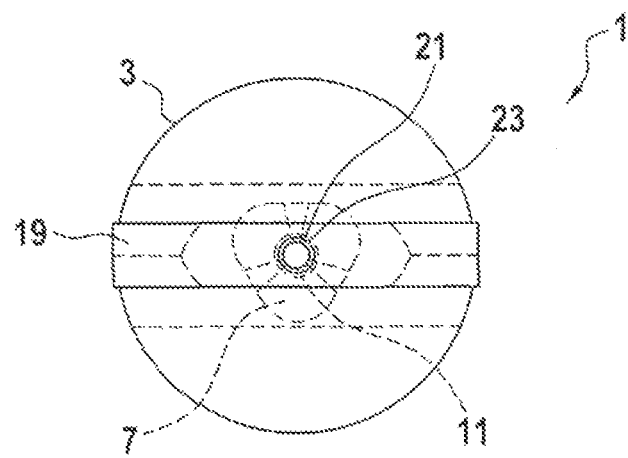

FIGS. 3a to 3c show various views of the transport device 31 without a container. The complementary handling unit 33 is preferably formed, as least in some areas, with a shape matching that of the handling unit 11 of the container 1. In this respect, the complementary handling unit 33 may include a receptacle 37 or a recess 37, into which the handling unit 11 of the container 1 can be introduced, at least in some areas, along an insertion direction E.

In particular, the complementary handling unit 33 may be formed as a clamp 33, wherein the handling unit 11 of the container 1 can be introduced into the open clamp 33, which after the insertion of the handling unit 11 can be closed and locked or arrested, and the locking or arresting may be carried out by means of a locking unit 33a, for example by means of a screw 33a that secures the pivotable part of the clamp 33.

The transport device 31 preferably comprises a motorized lifting device that can displace the complementary handling unit 33 along the lifting direction H, in particular along the vertical. The lifting device may for example be electrically driven via a chain or a spindle and/or hydraulically and/or pneumatically. Alternatively, the lifting device may also be manually driven.

Further preferably, the transport device 31 has a motorized rotation device 35, by means of which the complementary handling unit, preferably including a container 1 held thereon, can be rotated about the horizontal axis A. Alternatively, the rotation may also be carried out manually.

The transport device 31 is provided with wheels 39 and can therefore be moved, in particular moved in a motorized manner. To this end, the transport device 31 may have a drive for at least one wheel 39. The drive may for example be carried out electrically. Alternatively or in addition, the transport device 31 may also be manually pushed.

FIGS. 4a to 4d show various views of the transport device 31 with a container 1 fixed thereto in the stretched mounting condition. FIGS. 5a to 5d show various views of the container 1 in the mounting condition. As a result of the release of the securing unit 19 or of the strap 19, for example by releasing or unhooking the strap 19 from the securing unit attachment areas 21 on the baseplate 25, the container 1 is stretched at least in some areas due to the effect of gravity along the stretching direction S, which is preferably orientated parallel to the vertical.

In the embodiment shown, the securing unit 19 or the strap 19 is still fixed to the handling unit 11, so that it is connected to the container 1 in a captive manner and can be reused after usage of the container 1. The stretching of the container 1, i.e. the transition of the container from the initial condition to the mounting condition, may be carried out outside or within the holding device (not shown) for the container 1. During use, the container is substantially in the condition shown in FIGS. 5a to 5d, and during use the container is as a rule filled with a fluid.

Figure 6A:
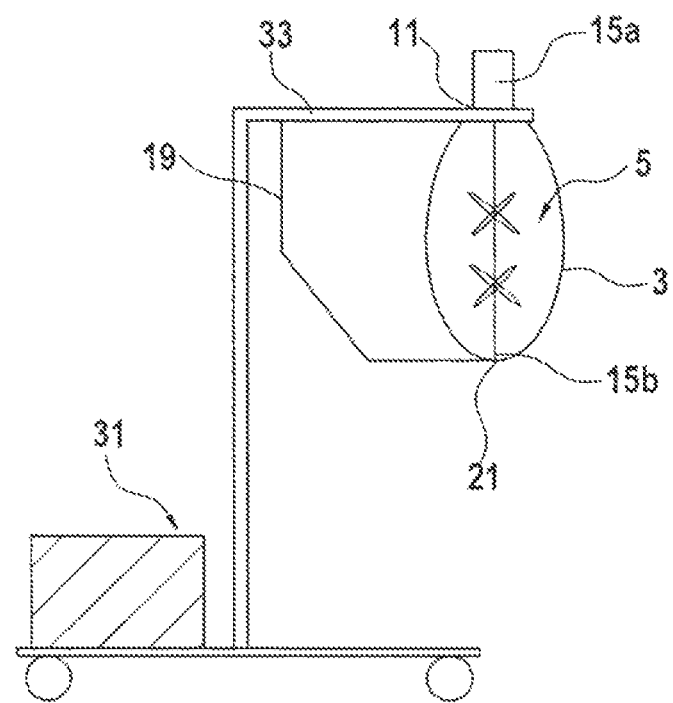
FIG. 6a shows a lateral view of a transport device with a container fixed thereto.
Figure 6B:
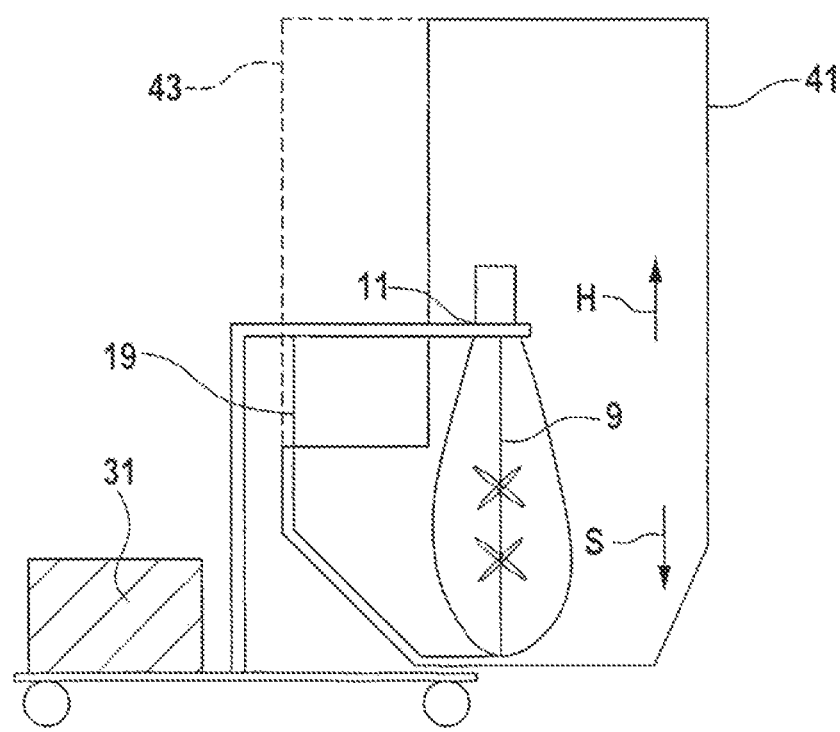
FIG. 6b shows a lateral view of the transport device during insertion of the container into a holding device.
Figure 6C:
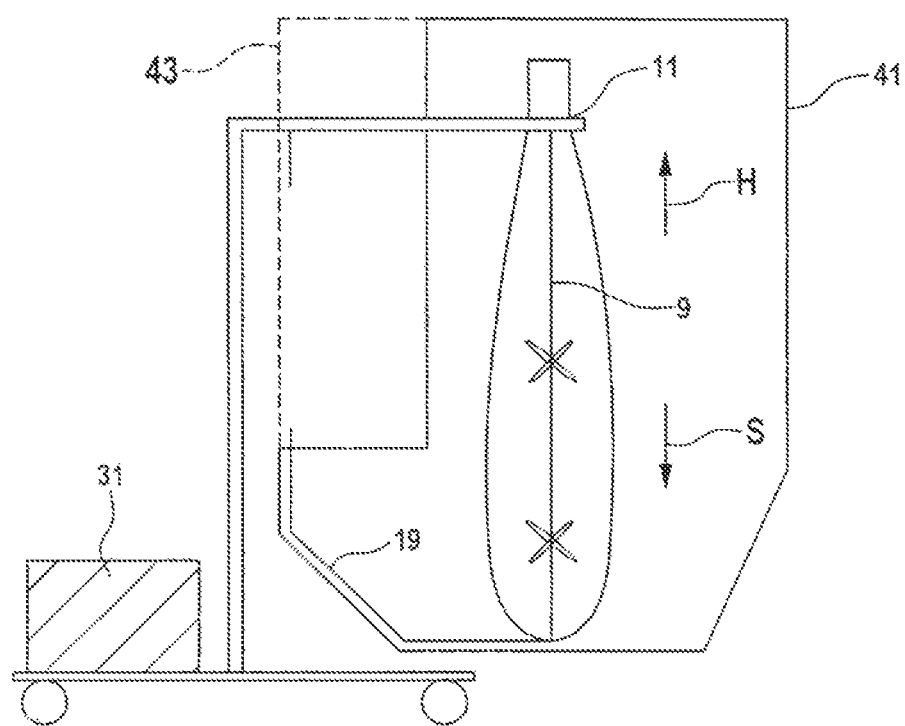
FIG. 6c shows a lateral view of the transport device during stretching of the container in the holding device.

FIGS. 6a to 6c show the transport device 31 with a container 1 fixed thereto during the insertion of the container into a holding device 41.

As shown in FIG. 6a, in the transport condition, the container 1 is moved by means of the transport device 31 from a storage place of the container 1 to the holding device 41 (shown in FIGS. 6b and 6c) and is lifted along the lifting direction H to such a degree that the container 1 can be placed in the holding device 41. The container is secured in the transport condition by means of a rigid securing unit 19 and the securing unit forms a rigid connection between a securing unit attachment area 21 provided at the bottom of the container 1 and the complementary handling unit 33 of the transport device 31.

As shown in FIG. 6b, the container 1 may be laterally inserted into the holding device 41. To this end, the holding device 41 has a lateral, in particular closable opening 43 in the wall of the holding device 41. The wall of the holding device 41 may for example be closable by means of a lateral door, through which the container 1 can, in the open condition of the door, be inserted into the holding device 41 and which can be closed once the container 1 has been inserted.

Once inserted into the holding device 41, the container 1 may be displaced within the holding device 41 in the direction opposite to the lifting direction H until the container 1 sits on the bottom of the holding device 41. In the course of this, the rigid securing unit 19 is introduced into the holding device 41 at the same time and is placed between the container 1 and the inner wall of the holding device 41, so that the securing unit 19 is again advantageously available, after usage of the container 1, for securing the container 1.

As shown in FIG. 6c, the release of the securing unit 19 from the complementary handling unit 33 of the transport device 31 can be carried out when the container is already mounted in the holding device. As a result of the release of the securing unit 19, the container 1 may be extended or stretched along the stretching direction S. The embodiment of the container 1 as shown in FIGS. 6a to 6c has a stirrer 5, the length of which is variable along the stretching direction S, and the shaft 9 of the stirrer is formed to be telescopic, so that its length can be varied.

Once the container 1 has been placed and stretched in the holding device 41, the complementary handling unit 33 can be released from the handling unit 11 of the container 1, in order to remove the transport device 31.

The released securing unit 19 remains on the container 1 and is located between the container 1 and the inner wall of the holding device 41. The rigid securing unit 19 may be formed with a profile, a hollow profile, a tube or a solid material of a metal or a plastic. In order to secure the securing unit 19 on the container 1, a complementary securing unit attachment area 23 (see also FIGS. 1, 2, 4 and 5) of the securing unit 19 may be fixed to the securing unit attachment area 21 of the container, which may preferably be provided on the bottom or on the baseplate of the container. As a result, the securing unit 19 may be connected to the container 1 in a captive manner.

Since the at least one securing unit 19 is formed to be rigid and is provided between the flexible container wall 3 and the inner wall of the holding device 41, the rigid securing unit 19 may push in the wall 3 of the flexible container 1 at least in some areas. During use of the container 1 and the stirrer 5 provided therein, the flow cross section of the fluid stirred in the container 1 may be locally reduced during stirring in the area of the wall 3 that is pushed in by the securing unit 19, so that in these places, the flow rate is locally increased, as a result of which turbulences are advantageously created, which leads to an improved mixing of the fluid.

Figure 7:
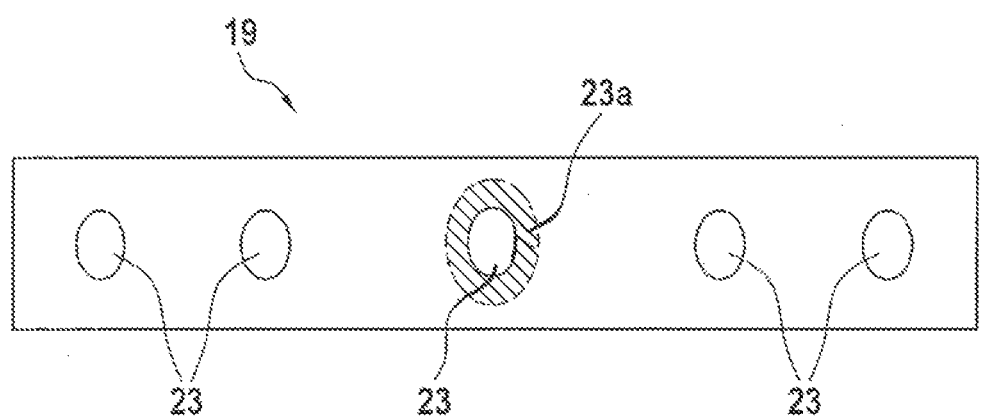
FIG. 7 shows an embodiment of the securing unit.

FIG. 7 shows a preferred embodiment of a securing unit 19 which is formed as a flexible strap. The securing unit 19 comprises a plurality of complementary securing unit attachment areas 23. A complementary securing unit attachment area 23 that is designed to come into engagement with a securing unit attachment area 21 at a bottom or a baseplate 15 of the container 1 (see FIGS. 1, 2, 4 and 5) may preferably include a reinforcement 23a. The reinforcement 23a may for example be formed by a material thickening or by at least one additional layer of the material of the strap 19. Advantageously, a mechanically particularly stress-resistant complementary securing unit attachment area 23 may be formed by the reinforcement 23a. The further complementary securing unit attachment areas 23 may be designed such that they come into engagement with associated securing unit attachment areas 21 on the handling unit 11 of the container or on the wall of the holding device 41.

It will be understood that instead of a strap, the securing unit 19 may alternatively be implemented as a cable, in particular with at least one loop, as a complementary securing unit attachment area 23, or as a linked chain, wherein the openings formed in the chain links may serve as a complementary securing unit attachment area 23.

LIST OF REFERENCE NUMERALS

1 Container
3 Wall
5 Stirrer
7 Stirrer blade
9 Shaft
9a, 9b Sub-shafts
11 Handling unit
13 Through-opening
15a Shaft bearing
15b Shaft bearing
17 Shaft coupling
19 Securing unit, strap
21 Securing unit attachment area
23 Complementary securing unit attachment area, hole

23a Reinforcement
25 Baseplate
31 Transport device
33 Complementary handling unit, clamp
33a Locking unit, screw
35 Rotation device
37 Receptacle
39 Wheel
41 Holding device
43 Opening in the holding device 41
A Axis
E Insertion direction
H Lifting direction
L Longitudinal direction of the strap 19
S Stretching direction of the container 1

The invention claimed is:

1. A bioreactor container (1) for inserting into a holding device, comprising:
 a wall (3) that is flexible at least in some areas, the wall being shortened, at least in some areas, in a transport condition in a direction opposite to a stretching direction (S);
 at least one securing unit attachment area (21) formed at one or more specified positions relative to the wall (3);
 a handling unit (11) connected to the wall (3) and designed to engage with a complementary handling unit (33) of a transport device (31);
 a securing unit (19) comprising a flexible non-stretchable strap (19) that is engageable with the wall (3) when the wall (3) is in the transport condition and prevents the wall (3) of the bioreactor container (1) from stretching along the stretching direction (S), the securing unit (19) having at least one hole (23) defining at least one complementary securing unit attachment area (23) that can be engaged with the at least one securing unit attachment area (21), wherein the container (1) can be extended at least in some areas along the stretching direction (S) when the securing unit (19) is released.

2. The bioreactor container (1) of claim 1, wherein the at least one securing unit attachment area (21) and the associated complementary securing unit attachment area (23) of the securing unit (19) are configured to hinder displacement of the securing unit (19) in a direction that is different from the stretching direction (S) when the at least one securing unit attachment area (21) and the associated complementary securing unit attachment area (23) are engaged.

3. The bioreactor container (1) of claim 2, wherein the at least one securing unit attachment area (21) comprises a securing unit attachment area (21) formed on a baseplate (25) that is located on a side of the wall (3) of the bioreactor container (1) that is opposite the handling unit (11) along the stretching direction (S).

4. The bioreactor container (1) of claim 1, wherein the strap (19) and the wall (3) of the bioreactor container (1) are made from the same material.

5. The bioreactor container (1) of claim 1, wherein the securing unit (19) is fixed to the wall (3) at least in some areas.

6. The bioreactor container (1) of claim 1, wherein the securing unit (19) comprises at least one rigid connection element that surrounds the wall (3) of the bioreactor container (1) at least in some areas.

7. The bioreactor container (1) of claim 1, wherein the at least one securing unit (19) is reusable to secure the bioreactor container (1) after use and after squashing in the direction opposite to the stretching direction (S) in the transport condition.

8. The bioreactor container (1) of claim 1, wherein the handling unit (11) comprises a shaft coupling (17) to connect a shaft (9) provided within the bioreactor container (1) to a drive provided outside of the bioreactor container (1).

* * * * *